(12) United States Patent
Sinnreich et al.

(10) Patent No.: US 8,241,303 B2
(45) Date of Patent: Aug. 14, 2012

(54) SURGICAL STAPLE REMOVER

(75) Inventors: Mark Sinnreich, Miami Beach, FL (US); Matthew Sinnreich, Miami Beach, FL (US); William Sinnreich, Boynton Beach, FL (US); Michael J. Mijares, Miami Lakes, FL (US)

(73) Assignee: Sinn Rx, LLC

( * ) Notice: Subject to any disclaimer, the term of this patent is extended or adjusted under 35 U.S.C. 154(b) by 0 days.

(21) Appl. No.: 13/225,278

(22) Filed: Sep. 2, 2011

(65) Prior Publication Data

US 2011/0319914 A1      Dec. 29, 2011

Related U.S. Application Data

(63) Continuation-in-part of application No. 13/045,509, filed on Mar. 10, 2011.

(60) Provisional application No. 61/312,327, filed on Mar. 10, 2010.

(51) Int. Cl.
*A61B 17/10* (2006.01)
(52) U.S. Cl. ........................................................ 606/138
(58) Field of Classification Search .................... 606/138
See application file for complete search history.

(56) References Cited

U.S. PATENT DOCUMENTS

| | | | | | |
|---|---|---|---|---|---|
| 1,948,096 | A | * | 2/1934 | Cavanagh | 254/28 |
| 4,026,520 | A | * | 5/1977 | Rothfuss et al. | 254/28 |
| 4,073,179 | A | * | 2/1978 | Hickey et al. | 72/409.17 |
| 4,515,348 | A | * | 5/1985 | Blake | 254/28 |
| D283,048 | S | * | 3/1986 | Sharkany | D24/133 |
| D287,279 | S | * | 12/1986 | Lazickas | D24/133 |
| 4,805,876 | A | * | 2/1989 | Blake et al. | 254/28 |
| 5,334,196 | A | * | 8/1994 | Scott et al. | 606/138 |
| D438,965 | S | * | 3/2001 | Porat | D24/133 |

* cited by examiner

*Primary Examiner* — Melanie Tyson
*Assistant Examiner* — Son Dang
(74) *Attorney, Agent, or Firm* — Mark Terry

(57) ABSTRACT

A surgical staple remover includes a first elongated element having a handle on one end and an upward sloped jaw element on the other end, wherein the jaw element comprises a pair of parallel jaws; a housing running a length of the first elongated element; an interior element within the housing comprising a planar element having a hook element; a second elongated element pivotally connected to the first elongated element and the interior element, such that moving the second elongated element results in moving the hook element and the jaw element while retracting the interior element, resulting in the hook element deforming the surgical staple so as to remove it and moving the surgical staple towards the housing; and a strip element located on top of the jaw element, such that when the hook element moves the removed surgical staple, the removed surgical staple is moved under the strip element.

20 Claims, 9 Drawing Sheets

SURGICAL STAPLE REMOVER

CROSS-REFERENCE TO RELATED APPLICATIONS

This patent application is a continuation-in-part of, and claims priority to, patent application Ser. No. 13/045,509, filed on Mar. 10, 2011 and entitled "Surgical Staple Remover," which further claims priority to provisional patent application No. 61/312,327, filed on Mar. 10, 2010 and entitled "Surgical Staple Remover." The subject matter of provisional patent application No. 61/312,327 and patent application Ser. No. 13/045,509 is hereby incorporated by reference in their entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention disclosed broadly relates to the field of medical devices, and more particularly relates to the field of devices for automating the process of removing surgical staples.

BACKGROUND OF THE INVENTION

The use of surgical staples in the medical industry for closing wounds or incisions in the skin of a patient has grown over the last decade due to its advantages over thread sutures. One of the main advantages of surgical staples over thread sutures is the reduced amount of time required for surgical staples to be implanted. In cases where large incisions are made, the use of surgical staples can, for example, reduce the length of time required for the suturing process and thus the length of time the patient must be maintained under anesthesia.

Conventional surgical staples comprise an elongated crown and an L-shaped portion on each end of the crown, wherein when implanted in a patient, the crown is located on the exterior of the skin of the patient and the L-shaped portions are bent in a downward direction so that the ends of the L-shaped portions are opposed, thereby incising and gripping the skin. The aforementioned conventional surgical staple may be removed from the skin of a patient by deforming the staple crown into a U-shaped configuration. This causes the L-shaped legs of the staple to shift upwardly and outwardly so that they may be lifted away from the patient's skin.

A conventional surgical staple remover 1, shown in FIG. 1, typically comprises a first handle 2 and a second handle 3 pivoted together at pivot point 11. Each handle includes circular finger inserts (4 and 5), each of which includes an orifice (6 and 7) for inserting a pair of fingers, such as a thumb and forefinger. The second handle 3 terminates in element 8 comprising two parallel, dual-pronged J-shaped units that are inserted under a surgical staple to be removed. The first handle 2 terminates in an anvil 10 that includes a downward facing footprint that is situated between the two units of the dual-pronged J-shaped element 8 and wherein the anvil 10 is placed on top of the crown of the surgical staple to be removed. When the conventional surgical staple remover 1 is gripped and contracted by a user, the downward facing footprint of anvil 10 applies force to the top of the crown of the surgical staple, thereby deforming the staple crown into a U-shaped configuration. Consequently, the L-shaped legs of the staple are moved upwardly and outwardly, thereby lifting away from the patient's skin.

One of the disadvantages of a conventional surgical staple remover is that it does not adequately deal with the final disposition of the surgical staple being removed. It is common to have surgical staples jump into the air or fall away during removal. Personnel must then go about finding and disposing of the removed surgical staple and sterilizing anything the staple came into contact with. It is unsanitary to allow removed surgical staples to come into contact with individuals or things since implanted surgical staples have resided within a human's body and may contain biologically hazardous residue that could contaminate individuals and locations. Further, the process of cleaning up after the conventional removal of surgical staples is time consuming and expensive since proper decontamination and sterilization procedures, employing the use of costly protective equipment and cleaning materials, must be undertaken. Further, during an operation on a patient, it is imperative that all removed staples are accounted for, lest the removed staple falls into an open incision unnoticed.

Another disadvantage of a conventional surgical staple remover is that it requires that each removed surgical staple is immediately disposed of. That is, the doctor or technician must remove a surgical staple, place it in a receptacle, and then return to the wound to remove the next surgical staple. This is problematic as it requires that the doctor or technician temporarily lose sight of the wound while he disposes of the removed surgical staple.

Therefore, a need exists to overcome the problems with the prior art as discussed above, and particularly for a more effective and efficient surgical staple remover, as well as a more sanitary and easy-to-operate surgical staple remover.

SUMMARY OF THE INVENTION

Briefly, according to an embodiment of the present invention, a surgical staple remover apparatus is disclosed. The surgical staple remover apparatus comprises:

(a) a first elongated element having a handle on one end and an upward sloped jaw element on the other end, wherein the jaw element comprises a pair of parallel jaws;

(b) a housing running a length of the first elongated element, beginning substantially at the jaw element and including an opening facing the jaw element;

(c) an interior element comprising a planar element having a hook element on one end, wherein the interior element is located within the housing such that the hook element extends out of the opening of the housing and wherein the interior element is secured to the housing with a spring;

(d) a second elongated element pivotally connected to the first elongated element and the interior element, such that moving the second elongated element into close proximity with the handle results in moving the hook element and the jaw element into close proximity while retracting the interior element into the housing, thereby resulting in the hook element pressing against a crown of a surgical staple, deforming the surgical staple so as to remove it and moving the surgical staple towards the housing; and (e) a strip element located on top of the jaw element, such that when the hook element deforms and moves the removed surgical staple towards the housing, the removed surgical staple is moved under the strip element and held in place by same.

The foregoing and other features and advantages of the present invention will be apparent from the following more particular description of the preferred embodiments of the invention, as illustrated in the accompanying drawings.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

DETAILED DESCRIPTION

The present invention solves problems with the prior art by providing a simple and easy-to-use surgical staple remover that automatically captures deformed and removed surgical staples. The apparatus of the present invention improves upon the prior art by definitively dealing with the final disposition of each surgical staple being removed. The present invention eliminates the possibility of having surgical staples jump into the air or fall away during removal. The present invention further eliminates the necessity for personnel to find and dispose of the removed surgical staple and sterilize anything the staple came into contact with. The present invention eradicates the potential for removed surgical staples to come into contact with, and contaminating, individuals or things. Further, the present invention eliminates the need to clean up after the conventional removal of surgical staples, thereby saving time and expense. Also, the present invention allows a doctor or technician to undergo the process of removing multiple surgical staples without losing sight of the wound during the process.

Finally, the present invention provides a surgical staple remover with a minimal number of component parts, thereby reducing the potential for failure or malfunction of the device. Also, the minimal number of component parts allows for quick and inexpensive fabrication of the surgical staple remover, thereby meeting the economic requirements for a disposable surgical staple remover. The present invention can be constructed of various metals, as well as plastic.

Figure 1:
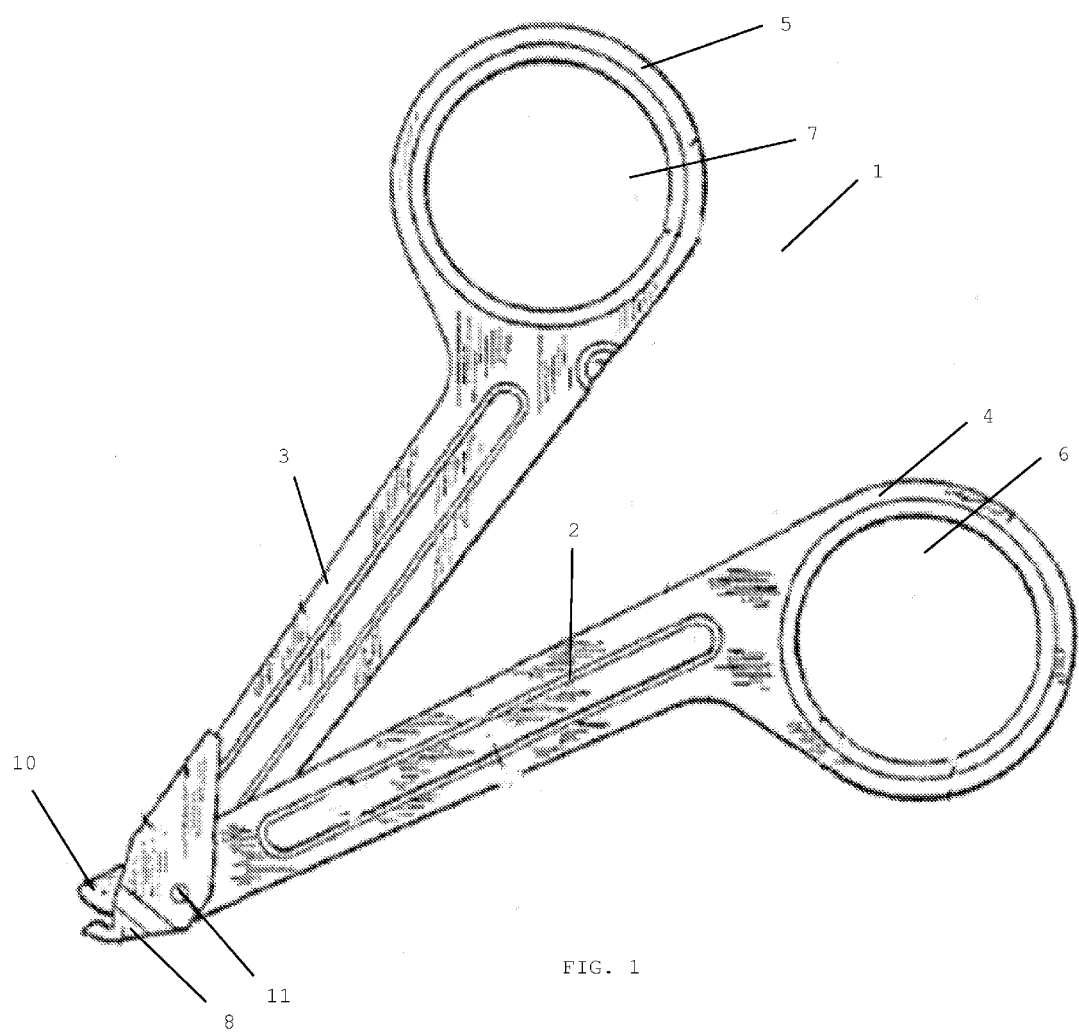
FIG. 1 is an illustration of a side view of a prior art surgical staple remover.
Figure 2:
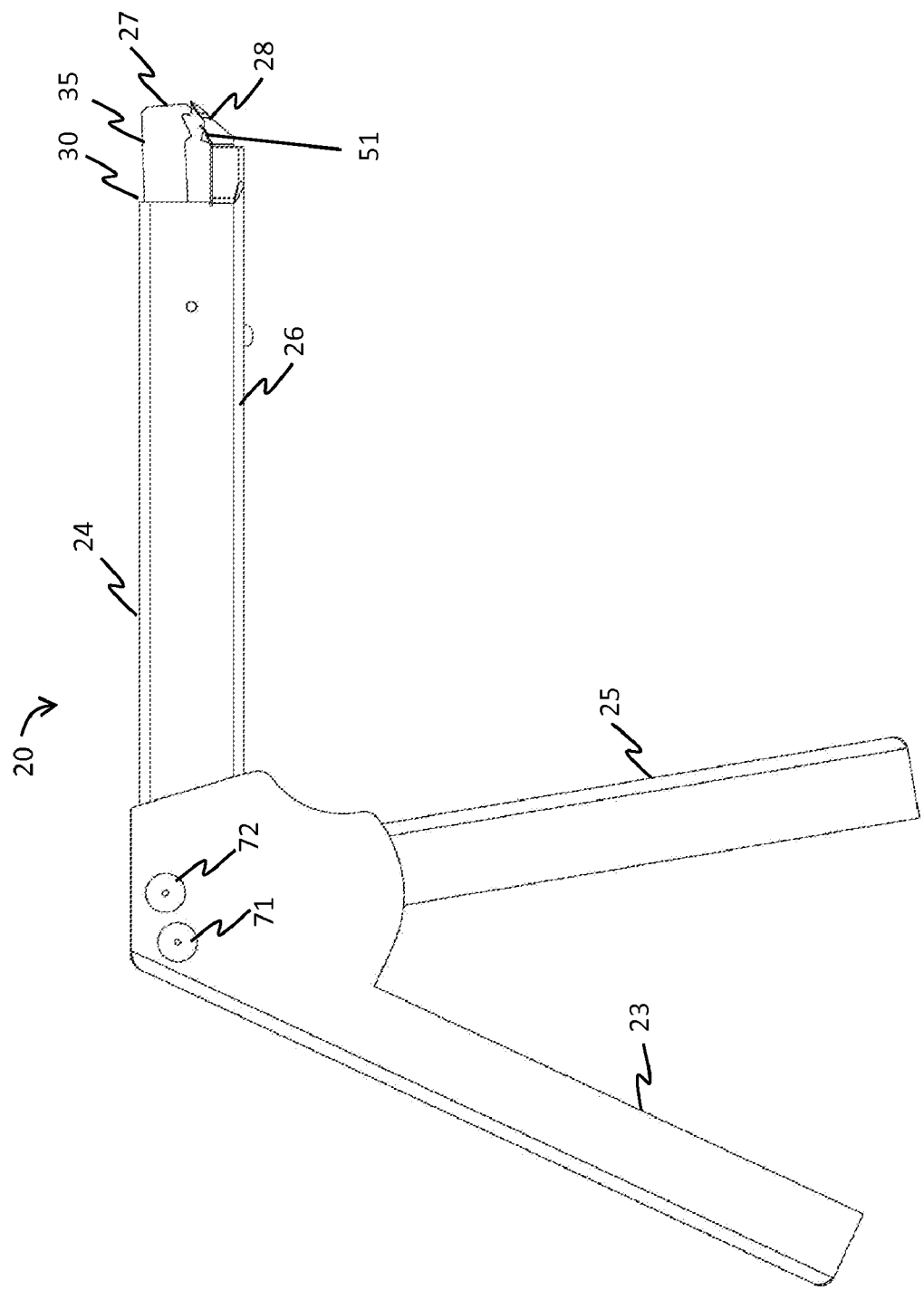
FIG. 2 is a side view of the surgical staple remover in an open position, in accordance with one embodiment of the present invention.

FIG. 2 is a side view of the surgical staple remover 20 in an open position, in accordance with one embodiment of the present invention. The apparatus 20 may be composed of a conventional medical device material such as stainless steel and other metal alloys, or a disposable material, such as plastic or a plastic derivative, so that the apparatus may be disposed after a single use, thereby eliminating the necessity for cleaning or sterilizing the apparatus between uses. One or more of the components that comprise the apparatus 20 may be stamp manufactured from a planar metallic sheet. See FIG. 8 which shows the components of the surgical staple remover 20. The low number of parts, especially moving parts, and the simplicity of the design results in a surgical staple remover 20 that is straightforward and inexpensive to fabricate, thereby meeting the requirements for a disposable medical device.

The apparatus 20 may include a first elongated element 24, otherwise known as the top element 24, to which a handle element 23 is affixed on a first end via joint elements 71 and 72. Note that the angle between top element 24 and handle element 23 may be substantially in the range of ninety degrees and one hundred thirty five degrees.

Top element 24 also includes a dual-toothed jaw element 28 protruding from the bottom portion of the second end of the element 24. The dual-toothed jaw element 28 may be integrally formed (such as via a stamping process) from the same continuous piece of plastic, metal or alloy (or the like) from which top element 24 is formed. The dual-toothed jaw element 28, seen in more detail in FIG. 3B, includes two parallel jaws 81 and 82 that point in an upward direction. The top surface of the jaws 81, 82 includes a dip or indentation 83, 84 in which a surgical staple is secured while it is deformed during removal. The dual-toothed jaw element 28 may have a size and shape that allows its complete insertion underneath a crown of a conventional surgical staple. The dual-toothed jaw element 28 may further be engineered to allow for slight lateral expansion to ease the deforming of the surgical staple.

Located within top element 24 is a wholly separate interior element 35 (described in greater detail below with reference to FIGS. 6, 7 and 8) that includes a downward facing hook element 27. The downward facing hook element 27 may comprise a curved element that protrudes downward from one end of the interior element 35, the tip of which includes a footprint for placement on top of a crown of a surgical staple. The hook element 27 serves to hook or grab the removed staple as it is retracted into the top element 24. Proximal to the hook element 27, the interior element 35 has a diagonal outline 58 (see FIG. 5) that slopes diagonally downward from the hook element 27 and ends in a point 59. This feature allows for greater consistency when removing multiple staples, one after another. The gap between the two parallel jaws 81 and 82 of jaw element 28 corresponds to, or accommodates, a profile of the hook element 27 (see FIG. 3B).

The hook element 27 and jaw element 28 work in concert to remove surgical staples. At rest, the hook element 27 is separated from the jaw element 28 so as to produce a space between the two items (see FIG. 3B). The apparatus 20 is maneuvered such that the jaw element 28 is placed underneath the crown of the surgical staple to be removed. The crown of the surgical staple to be removed rests within the dips or depressions 83, 84 of the jaws 81, 82. Upon compression of the apparatus 20, the hook element 27 is moved downward towards the jaw element 28 and is eventually moved in between the jaws 81, 82 of the jaw element 28. In so doing, the hook element 27 deforms the crown of the surgical staple such that the staple crown is bent into a U-shaped configuration, causing the L-shaped legs of the staple to shift upwardly and outwardly so that they may be lifted away from the patient's skin. Subsequently, the hook element 27 grabs the deformed and removed surgical staple and moves it underneath element 51 and in the direction of the top element 24.

The apparatus 20 may further include a second elongated element 25, otherwise known as the lever 25, wherein elements 24 and 25 are pivotally connected at pivot point 72 such that the angle between elements 25 and 23, as well as the angle between elements 25 and 24, may be changed. The angle between handle 23 and lever 25 is substantially forty five degrees and the angle between lever 25 and top element 24 is substantially eighty degrees.

The lever 25 is pivotally connected to the interior element 35 at pivot point 98 (see FIG. 6) such that squeezing the apparatus 20, or moving the lever 25 towards handle 23, results in moving the interior element 35 and hook element 27 back towards handle 23. Conversely, moving the lever 25 away from handle 23 results in moving the interior element 35 and hook element 27 outwards and away from handle 23.

The apparatus 20 may further include a housing 26 having an interior volume and running at least a portion of a length of the top element 24, beginning at the jaw element 28 and including an opening 30 facing the jaw element 28, such that surgical staples removed with the apparatus 20 are drawn into the housing 26. The housing 26 may comprise an elongated rectangular box running at least a portion of a length of the top element 24.

Figure 3A:
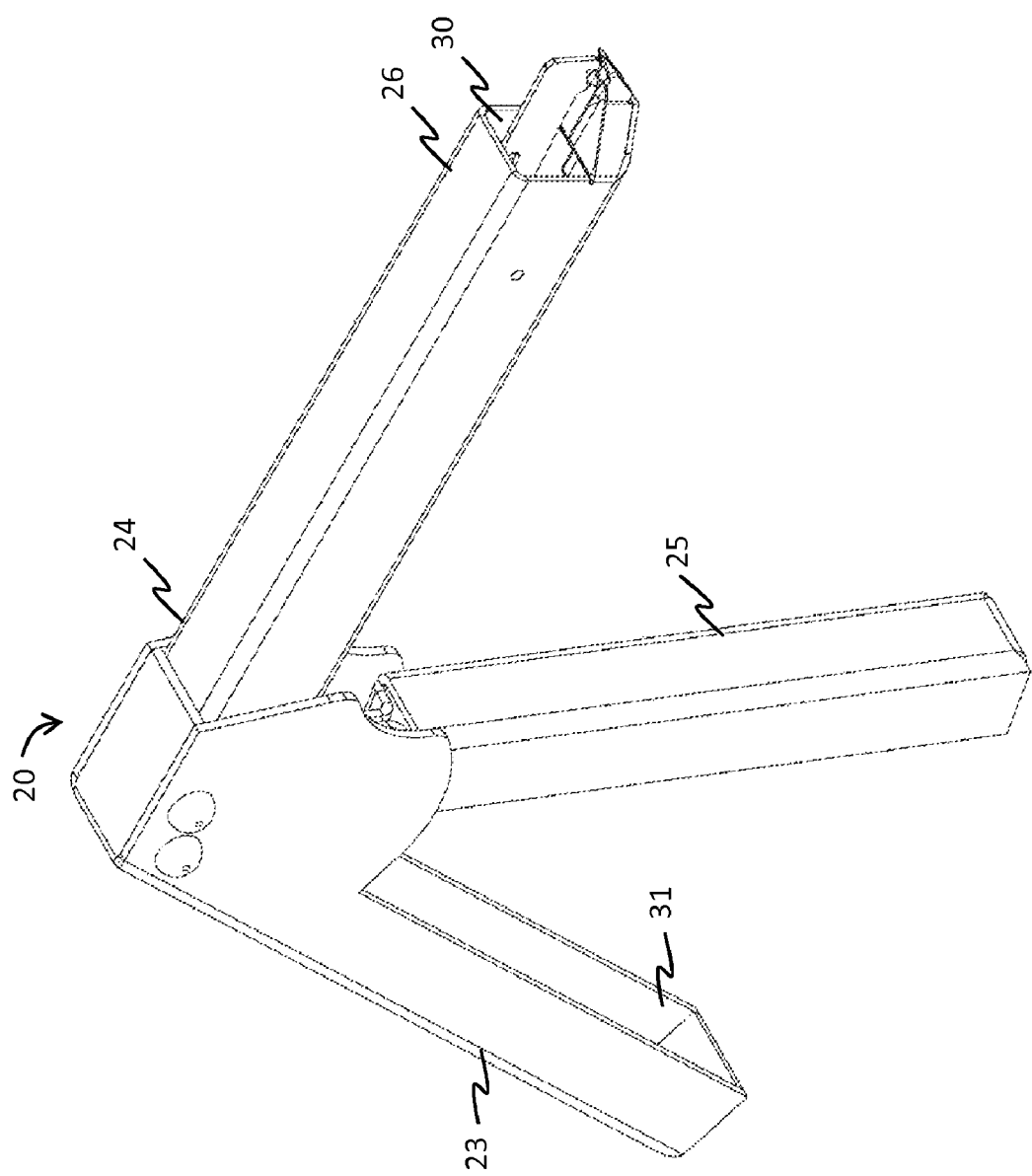
FIG. 3A is a perspective view of the surgical staple remover in an open position, in accordance with one embodiment of the present invention.
Figure 3B:
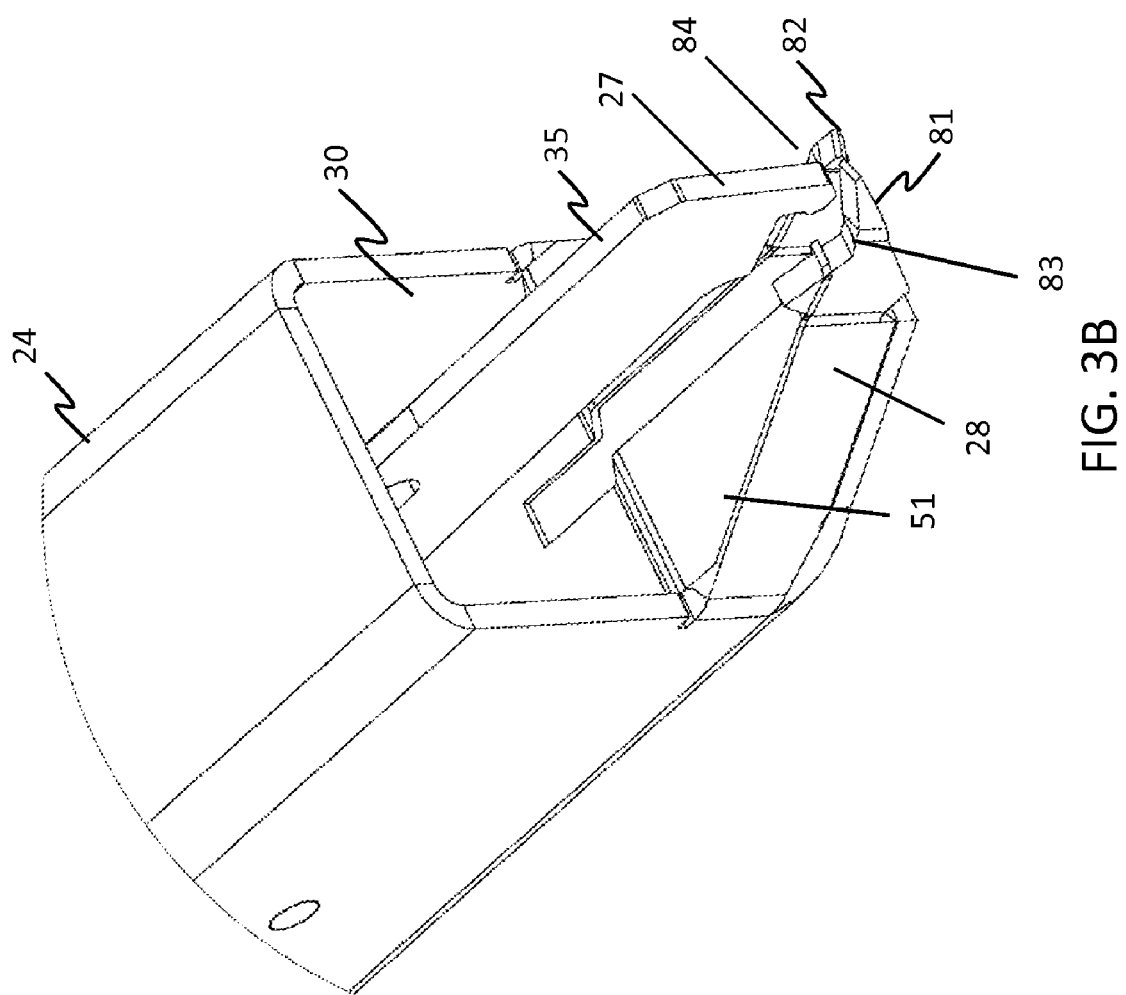
FIG. 3B is a more detailed perspective view of the front end of the surgical staple remover in an open position, in accordance with one embodiment of the present invention.

FIG. 2 also shows the strip element 51 extending, or protruding, from the opening 30 and on top of the jaw element 28 (see FIG. 3B for more detail). The action performed by the strip element 51 is described in greater detail below.

FIG. 3A is a perspective view of the surgical staple remover 20 in an open position, in accordance with one embodiment of the present invention. The perspective view of FIG. 3A shows a hollow area 31 within handle 23, wherein the hollow area 31 is sized to accommodate the lever 25 such that the lever 25 rests within the hollow area 31 when the lever 25 is moved towards and into the handle 23 (see FIG. 4 and FIG. 7). FIG. 3A also shows the opening 30 of housing 26. FIG. 3B is a more detailed perspective view of the surgical staple remover 20 in an open position, in accordance with one embodiment of the present invention.

Figure 4:
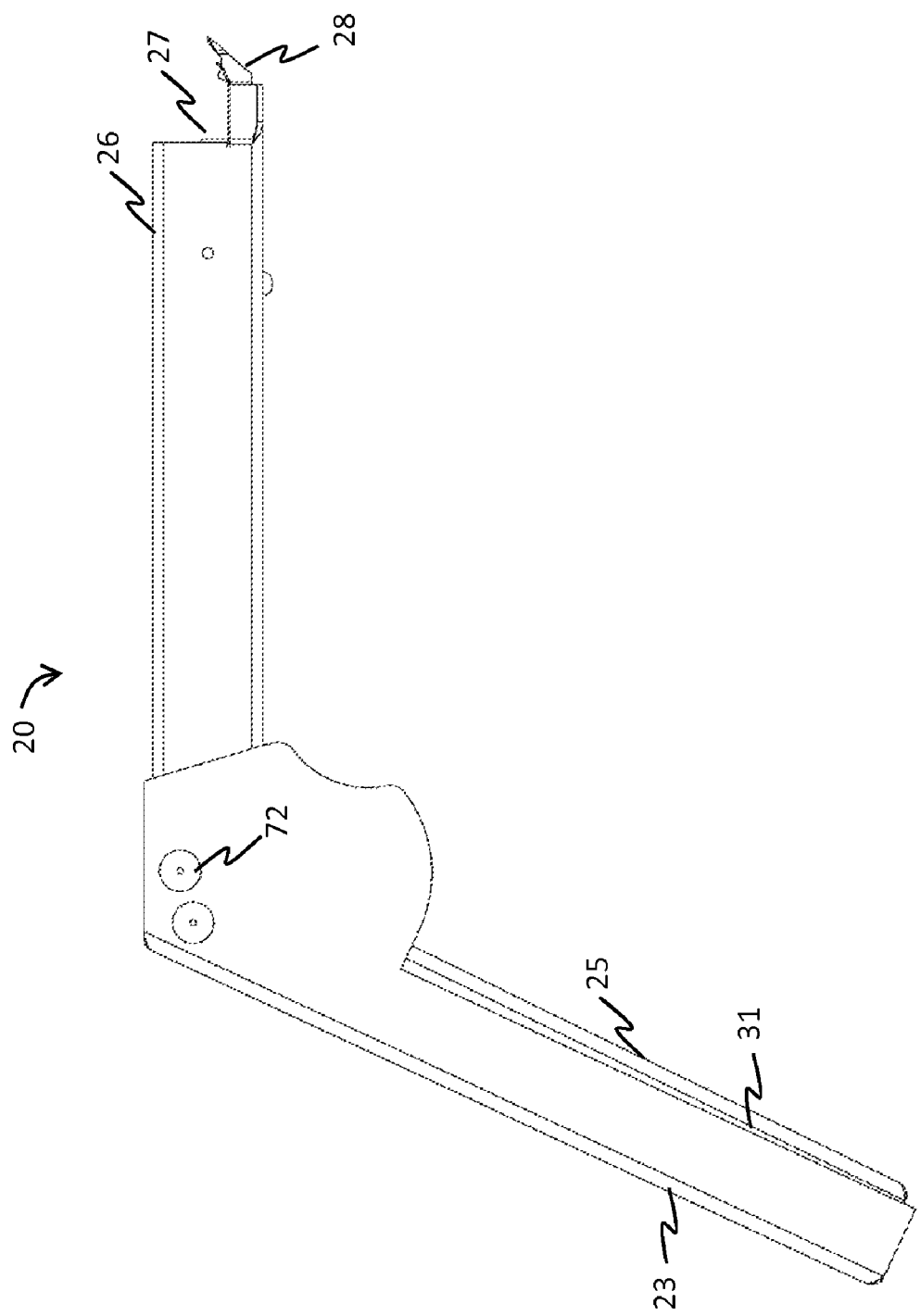
FIG. 4 is a side view of the surgical staple remover in a closed position, in accordance with one embodiment of the present invention.

FIG. 4 is a side view of the surgical staple remover 20 in a closed position, in accordance with one embodiment of the present invention. The side view of FIG. 4 shows the lever 25 has pivoted about pivot point 72 and moved towards and into hollow area 31 of handle 23, thereby moving hook element 27 downward between the jaws 81, 82 of jaw element 28 and retracting interior element 35 further into housing 26. The closing of the surgical staple remover 20 results in the deformation and removal of a surgical staple, as described in greater detail above. Although not shown in FIG. 4, in one embodiment the surgical staple remover 20 may include a miniature battery-powered LED on top of the housing 26, wherein the LED points at the service end of the apparatus 20 so as to illuminate the area surrounding the staple being removed.

Figure 5:
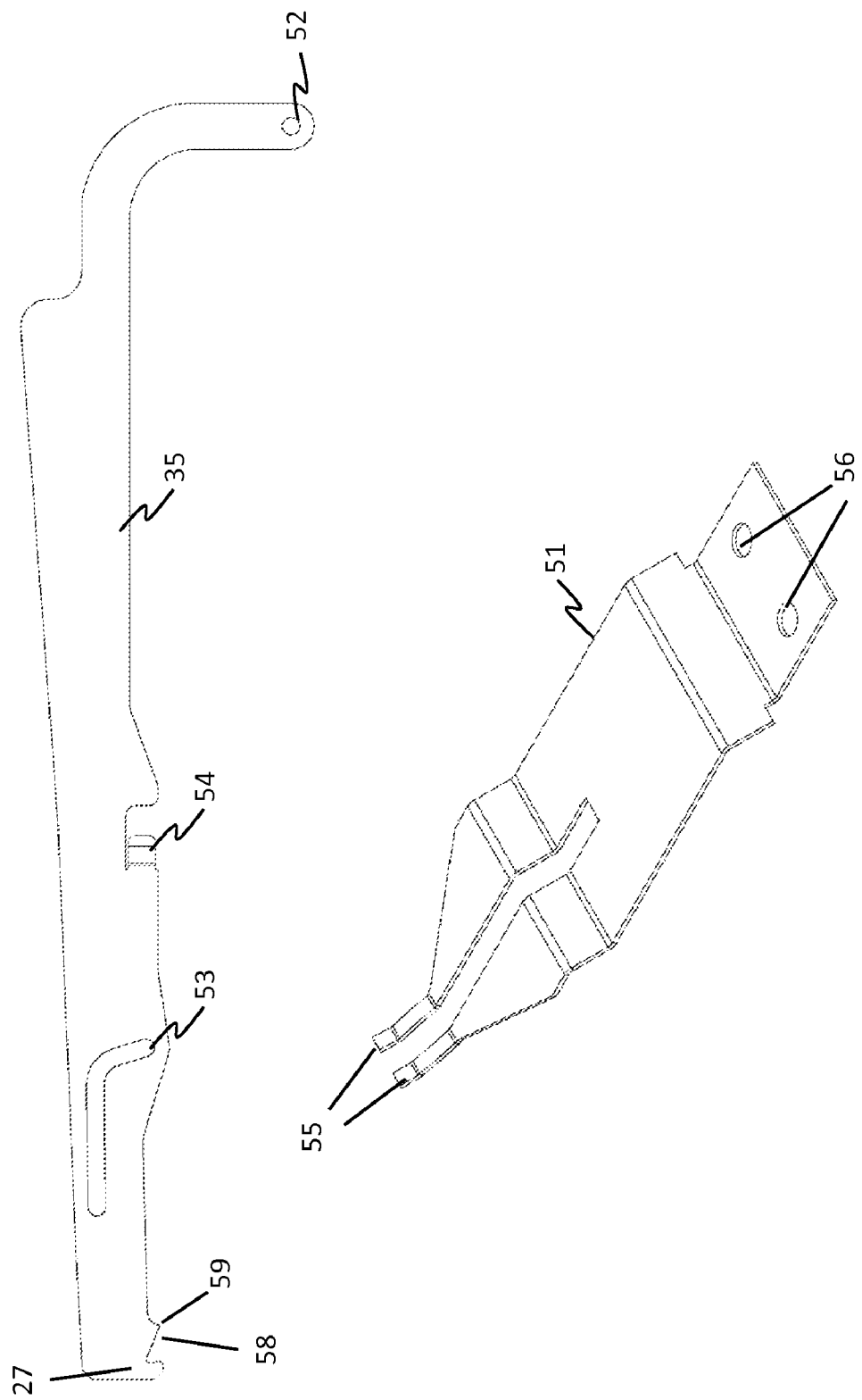
FIG. 5 is a perspective view of two interior components of the surgical staple remover apparatus, in accordance with one embodiment of the present invention.

FIG. 5 is a perspective view of the interior element 35 and strip element 51 of the surgical staple remover apparatus 20, in accordance with one embodiment of the present invention. The perspective view of FIG. 5 shows the interior element 35, which is located in the housing 26, having a hook element 27 on a distal end. On the proximal end, element 35 includes an orifice 52 which is utilized to secure the interior element 35 to lever 25 at joint 98. Element 35 also includes a cutout 53 that comprises a curved shape travelling straight along the length of elongated element 35 from the distal end to the proximal end and then downward. The cutout 53 is utilized as a track to control the height of the interior element 35 as it retracts into the housing 26 when the lever 25 is squeezed. This feature is described in greater detail below. Element 35 also includes a tab 54 that comprises a piece of the surface of the element 35 that protrudes in a proximal direction so as to provide a hook-like feature for a spring, which is described in greater detail below.

FIG. 5 shows that strip element 51 includes dual pronged jaw element 55, which minors the jaw element 28 of the top element 24, such that jaw element 55 is curved upwards. FIG. 3B shows that the strip element 51 is located on a bottom interior surface of the housing 26 and extends on top of jaw element 28 such that there is a narrow space between jaw element 28 and strip element 51 to allow the removed and deformed staple to be held securely in the removal and storage process. When the hook element 27 moves a removed surgical staple into the housing 26, the removed surgical staple is moved under the strip element 51 and held in place between the jaw element 28 and strip element 51. Note the strip element 51 is secured to the bottom interior surface of the housing 26 via a fastener inserted through orifices 56 (see FIG. 8). The strip element 51 may comprise a strip of a shape memory alloy that includes one or more bends.

The process of utilizing the surgical staple remover apparatus 20 according to one embodiment of the present invention will now be described with reference to FIGS. 6-8. First, FIG. 8 shows that pins or rivets 93 may be used to hingably connect the handle 23 to the top element 24 in joints 71 and 72, and to hingably connect the lever 25 to the top element 24. Likewise, note that lever 25 includes an orifice 61, which is hingably connected to the interior element 35 at orifice 52. Also, pin or rivets 95 may be used to couple the strip element 51 to the bottom interior surface of the housing 26 of top element 24. Also shown in FIG. 8 is a rod assembly 92 comprising of two hollow cylindrical elements through which a pin is extended. Assemblage of the apparatus 20, namely, the rod assembly 92, comprises placing one of the hollow cylindrical elements on each side of the cutout 53 and then inserting the pin through the first hollow cylindrical element, through the cutout 53 and then through the second hollow cylindrical element. This arrangement prevents the interior element 53 from moving laterally, or side-to-side, when the interior element 35 is moving lengthwise into or out of the housing 26. Lateral stability is desirable when surgical staples are being removed.

Figure 6:
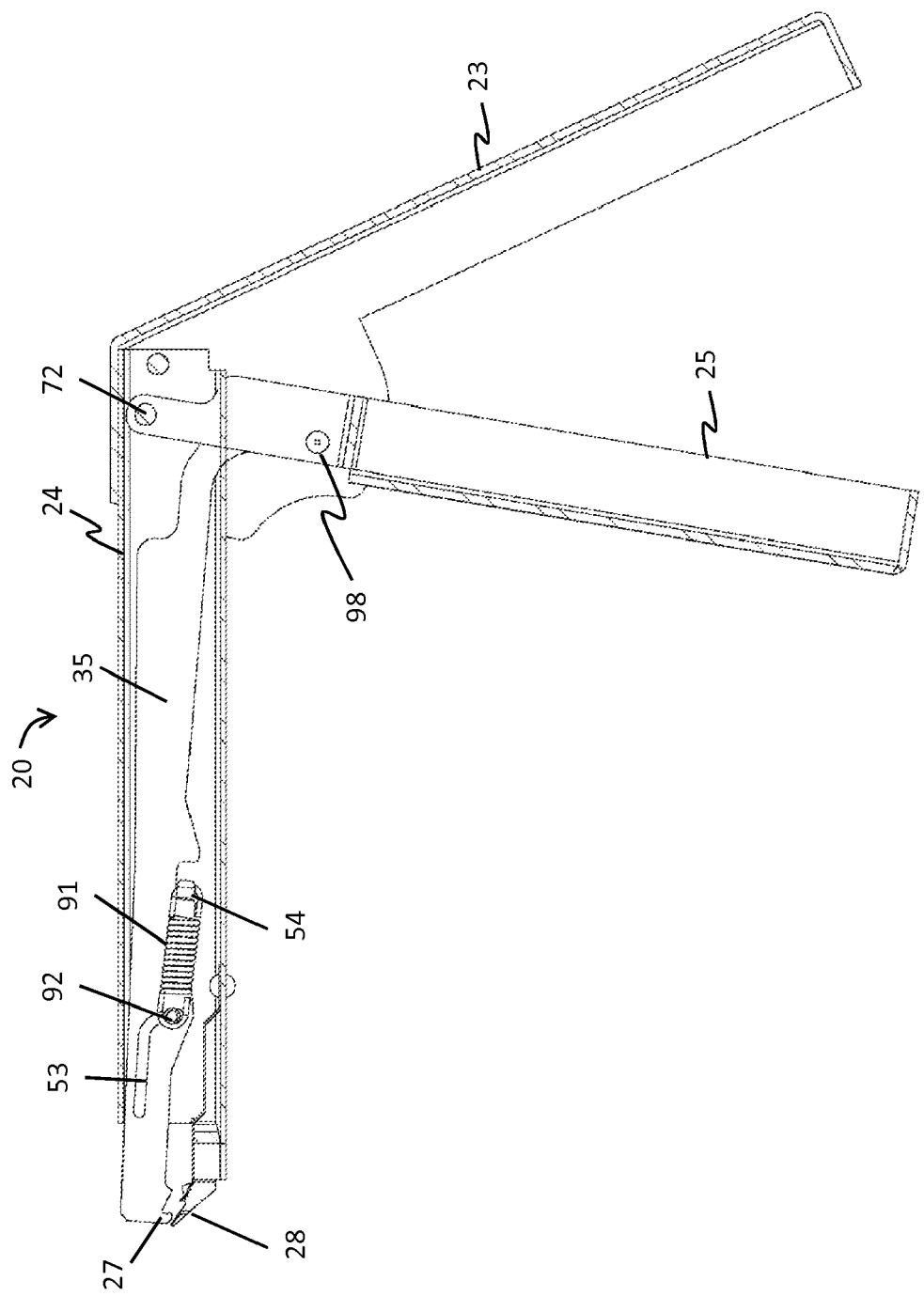
FIG. 6 is a cross-sectional view of the surgical staple remover in an open position, in accordance with one embodiment of the present invention.

FIG. 6 is a cross-sectional view of the surgical staple remover 20 in an open position. FIG. 6 shows that the proximal end of spring 91 is connected to interior element 35 at tab 54 and the distal end of spring 91 is connected to the housing 26 of top element 24 at bolt assembly 92. Note also that bolt assembly 92 extends through the cutout 53 of interior element 35. In the open position of FIG. 6, the jaw element 28 of surgical staple remover 20 is placed under a surgical staple. At this point, the apparatus 20 is ready to remove the staple and pull it into the housing 26 when the surgical staple remover 20 moves into a closed position.

Figure 7:
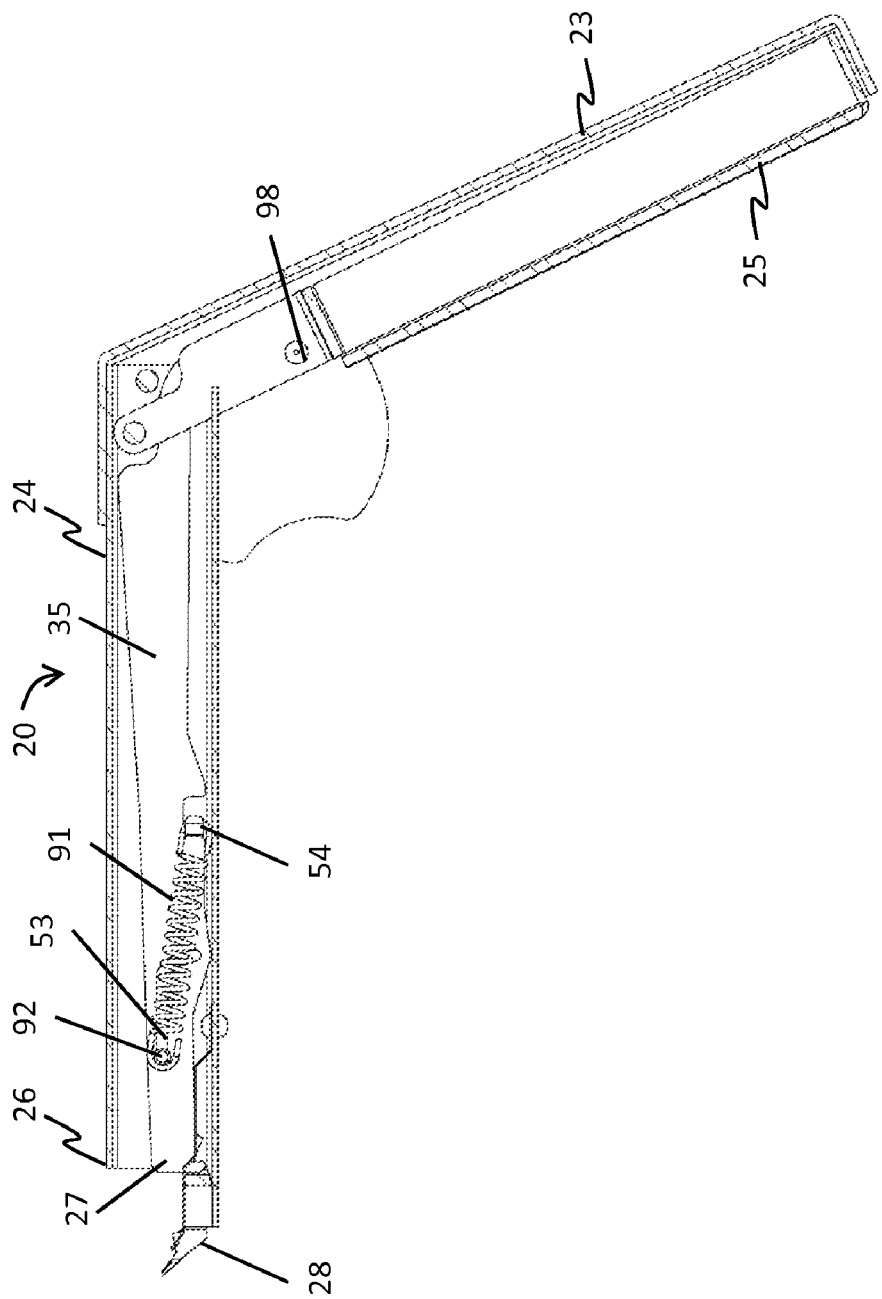
FIG. 7 is a cross-sectional view of the surgical staple remover in a closed position, in accordance with one embodiment of the present invention.
Figure 8:
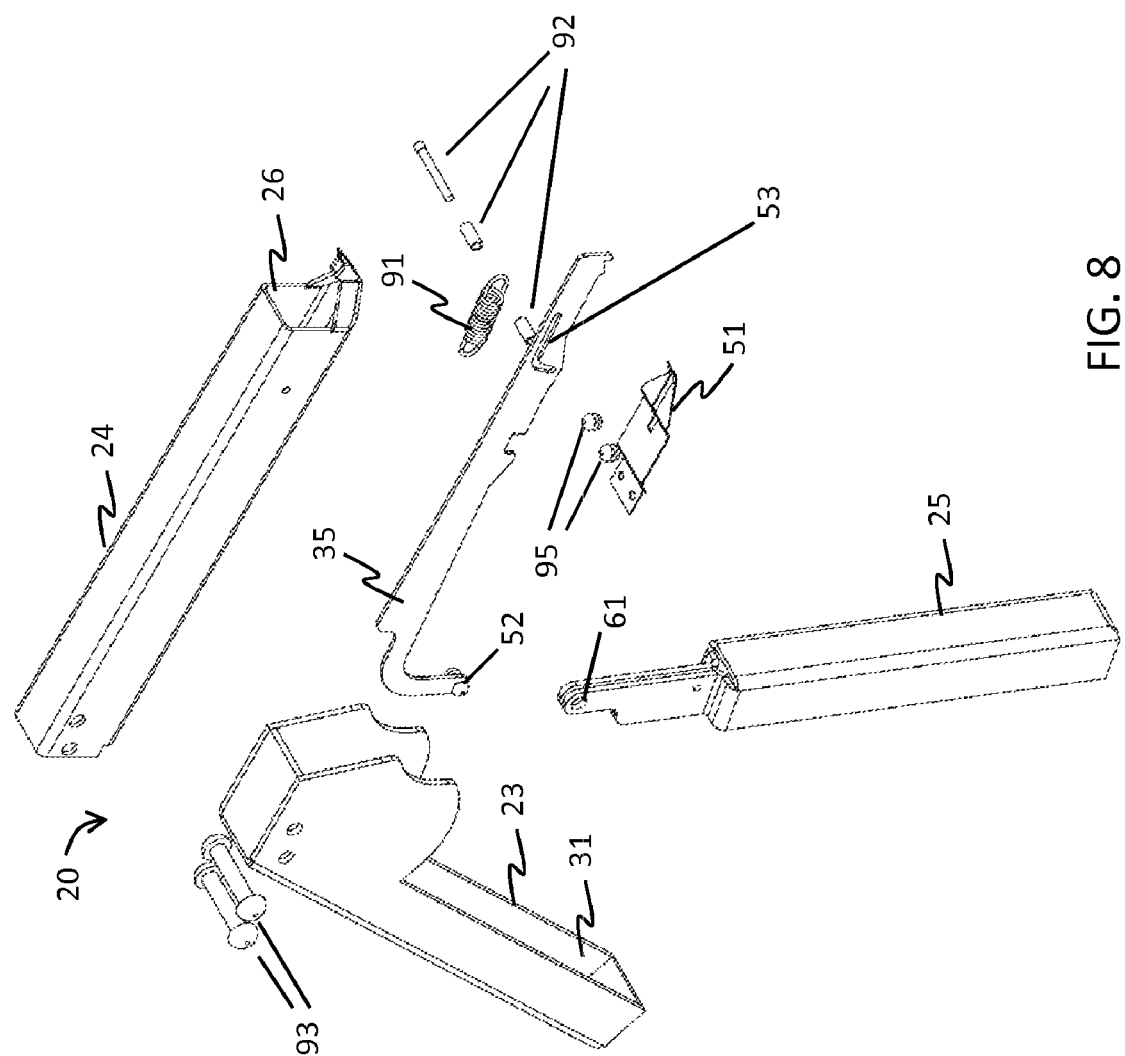
FIG. 8 is a perspective view of the surgical staple remover in a disassembled state, in accordance with one embodiment of the present invention.

FIG. 7 is a cross-sectional view of the surgical staple remover 20 in a closed position. As the lever 25 is squeezed and brought together with handle 23, lever 25 pulls interior element 35 back (via joint 98). At the same time interior element 35 is being pulled back into housing 26, the interior element 35 moves downward, since interior element 35 follows the track defined by cutout 53. Recall that bolt assembly 92, a stationary element affixed to top element 24, extends through the cutout 53 of interior element 35. The movement of interior element 35 moves the hook element 27 into the gap between the jaws 81, 82 of jaw element 28 and then towards the opening 30 of the housing 26. This movement results in the hook element 27 deforming the surgical staple for removal and, subsequently, the hook element 27 grabbing and pulling the deformed staple underneath the strip element 51 towards the opening 30 of the housing 26. The strip element 51 may hold a plurality of removed surgical staples in between the narrow gap between the element 51 and jaw element 28. In this manner, multiple surgical staples can be quickly and easily removed, and securely captured by, the apparatus 20.

Note that in the closed position, the spring 91 has been elongated. In this position, the spring 91 possesses potential energy as it is placed under tension. Consequently, when the lever 25 is released by the user, the spring 91 pulls the interior element 35 back out of the housing 26 and into the open position. Since the interior element 35 is connected to the lever 25 at joint 98, the lever 25 is also moved back to its open position by the spring 91.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

The invention claimed is:

1. A surgical staple remover apparatus, comprising:
   a first elongated element having a handle on one end and an upward sloped jaw element on the other end, wherein the jaw element comprises a pair of parallel jaws;
   a housing running a length of the first elongated element, beginning substantially at the jaw element and including an opening facing the jaw element;
   an interior element comprising a planar element having a hook element on one end, wherein the interior element is located within the housing such that the hook element extends out of the opening of the housing and wherein the interior element is secured to the housing with a spring;
   a second elongated element pivotally connected to the first elongated element and the interior element, such that moving the second elongated element into close proximity with the handle results in moving the hook element and the jaw element into close proximity while retracting the interior element into the housing, thereby resulting in the hook element pressing against a crown of a surgical staple, deforming the surgical staple so as to remove it and moving the surgical staple towards the housing; and
   a strip element located on top of the jaw element, such that when the hook element deforms and moves the removed surgical staple towards the housing, the removed surgical staple is moved under the strip element and held in place by same.

2. The surgical staple remover apparatus of claim 1, wherein the hook element comprises a hook element that protrudes downward from a tip of the first elongated element.

3. The surgical staple remover apparatus of claim 2, wherein the jaw element comprises a size and shape that allows its complete insertion underneath a crown of a surgical staple.

4. The surgical staple remover apparatus of claim 3, wherein a gap between the parallel jaws of the jaw element corresponds to a profile of the hook element.

5. The surgical staple remover apparatus of claim 4, wherein the second elongated element is pivotally connected to the interior element at a pivot point that is lower than the pivot point to which the second elongated element is connected to the second elongated element.

6. The surgical staple remover apparatus of claim 5, wherein the housing comprises an elongated substantially rectangular box running a length of the first elongated element, beginning at the jaw element and including an opening facing the jaw element.

7. The surgical staple remover apparatus of claim 6, wherein the interior element includes a cutout that runs a portion of a length of the interior element.

8. The surgical staple remover apparatus of claim 7, wherein the housing includes a stationary rod that extends through the cutout.

9. The surgical staple remover apparatus of claim 8, wherein the interior element includes a tab for securing the spring to the interior element.

10. The surgical staple remover apparatus of claim 9, wherein the spring is connected on a first end to the tab of the interior element and wherein the spring is connected on a second end to the rod of the housing.

11. The surgical staple remover apparatus of claim 10, wherein the strip element includes a gap that corresponds to a profile of the hook element.

12. The surgical staple remover apparatus of claim 11, wherein the strip element comprises a shape memory alloy that includes one or more bends.

13. The surgical staple remover apparatus of claim 12, wherein the apparatus is composed of any one of stainless steel, a metal alloy, plastic, or a plastic derivative.

14. The surgical staple remover apparatus of claim 12, wherein the apparatus is composed of a disposable material.

15. A surgical staple remover apparatus, comprising:
   a first elongated element having a handle on one end and an upward sloped jaw element on the other end, wherein the jaw element comprises a pair of parallel jaws having a gap between the parallel jaws;
   a housing running comprising a rectangular box running substantially a length of the first elongated element, beginning substantially at the upward sloped jaw element and including an opening facing the jaw element;
   an interior element comprising a planar element having a hook element on one end, wherein the interior element is located within the housing such that the hook element extends out of the opening of the housing and wherein the interior element is secured to the housing with a spring;
   a second elongated element pivotally connected to the first elongated element at a first pivot point and the interior element at a second pivot point, such that moving the second elongated element into close proximity with the handle results in moving the hook element and the jaw element into close proximity while retracting the interior element into the housing, thereby resulting in the hook element pressing against a crown of a surgical staple, deforming the surgical staple so as to remove it and moving the surgical staple towards the housing; and a strip element located on top of the jaw element, such that when the hook element deforms and moves the removed surgical staple towards the housing, the removed surgical staple is moved under the strip element and held in place by same.

16. The surgical staple remover apparatus of claim 15, wherein the interior element includes a cutout that runs a portion of a length of the interior element.

17. The surgical staple remover apparatus of claim 16, wherein the housing includes a stationary rod that extends through the cutout.

18. The surgical staple remover apparatus of claim 17, wherein the interior element includes a tab for securing the spring to the interior element.

19. The surgical staple remover apparatus of claim 18, wherein the spring is connected on a first end to the tab of the interior element and wherein the spring is connected on a second end to the rod of the housing.

20. The surgical staple remover apparatus of claim 19, further comprising an LED positioned on top of the housing and arranged so as to illuminate an area distal to the jaw element.

* * * * *